(12) United States Patent
Kaffka

(10) Patent No.: US 10,596,574 B2
(45) Date of Patent: Mar. 24, 2020

(54) INCUBATION TRAY

(71) Applicant: Euroimmun Medizinische Labordiagnostika AG, Luebeck (DE)

(72) Inventor: Christian Kaffka, Dassow (DE)

(73) Assignee: Euroimmun Medizinische Labordiagnostika AG, Luebeck (DE)

( * ) Notice: Subject to any disclaimer, the term of this patent is extended or adjusted under 35 U.S.C. 154(b) by 165 days.

(21) Appl. No.: 15/563,720

(22) PCT Filed: Dec. 21, 2015

(86) PCT No.: PCT/EP2015/002575
§ 371 (c)(1),
(2) Date: Oct. 2, 2017

(87) PCT Pub. No.: WO2016/169576
PCT Pub. Date: Oct. 27, 2016

(65) Prior Publication Data
US 2018/0078941 A1  Mar. 22, 2018

(30) Foreign Application Priority Data
Apr. 24, 2015 (EP) .................................... 15001230

(51) Int. Cl.
*B01L 9/00* (2006.01)
*G01N 1/31* (2006.01)

(52) U.S. Cl.
CPC ......... *B01L 9/52* (2013.01); *B01L 2300/0822* (2013.01); *B01L 2300/0877* (2013.01); *B01L 2400/049* (2013.01); *G01N 1/312* (2013.01)

(58) Field of Classification Search
CPC ............... B01L 9/52; B01L 2300/0822; B01L 2300/0877; B01L 2400/049; G01N 1/312
(Continued)

(56) References Cited

U.S. PATENT DOCUMENTS 5,073,504 A * 12/1991 Bogen .................... G01N 1/312
422/523
5,922,604 A 7/1999 Stapleton et al.
(Continued)

FOREIGN PATENT DOCUMENTS

DE   20 2011 005 278 U1   11/2012
EP        2 660 602        11/2013
(Continued)

OTHER PUBLICATIONS

International Search Report dated Mar. 23, 2016 in PCT/EP2015/002575 filed Dec. 21, 2015.
(Continued)

*Primary Examiner* — Jill A Warden
*Assistant Examiner* — Jacqueline Brazin
(74) *Attorney, Agent, or Firm* — Grüneberg and Myers PLLC

(57) ABSTRACT

The invention relates to an incubation tray having a depression formed by the walls of the incubation tray and having a base, wherein the incubation tray has a means for drawing off liquid on at least one longitudinal end of the depression, preferably an opening which opens into an outlet channel on the longitudinal end of the depression, particularly preferably in a wall of the incubation tray, wherein the opening and the outlet channel are designed such that negative pressure can be applied, wherein the incubation tray is pivotable about the transverse axis of the incubation tray, and wherein the incubation tray can be equipped with a support.

16 Claims, 6 Drawing Sheets

(58) Field of Classification Search
USPC .......................................................... 422/551
See application file for complete search history.

(56) References Cited

U.S. PATENT DOCUMENTS

| | | | |
|---|---|---|---|
| 6,673,620 B1* | 1/2004 | Loeffler | B01L 3/502 |
| | | | 359/398 |
| 7,476,543 B2* | 1/2009 | Becker | G01N 1/2813 |
| | | | 422/561 |
| 2004/0001779 A1 | 1/2004 | Anderson et al. | |
| 2004/0086428 A1 | 5/2004 | Loeffler et al. | |
| 2004/0101870 A1 | 5/2004 | Caubet et al. | |
| 2005/0239195 A1* | 10/2005 | Oram | B01L 3/502 |
| | | | 435/288.3 |
| 2008/0056954 A1 | 3/2008 | Loeffler et al. | |
| 2009/0018034 A1 | 1/2009 | Anderson et al. | |
| 2010/0284859 A1* | 11/2010 | Cooney | B01J 19/0046 |
| | | | 422/68.1 |
| 2011/0044865 A1* | 2/2011 | Groisman | B01L 9/527 |
| | | | 422/503 |
| 2012/0201723 A1 | 8/2012 | Loeffler et al. | |
| 2014/0186971 A1 | 7/2014 | Winfried et al. | |
| 2014/0248618 A1 | 9/2014 | Shaikh et al. | |
| 2019/0368983 A1* | 12/2019 | Einsle | B01L 1/025 |

FOREIGN PATENT DOCUMENTS

| | | | |
|---|---|---|---|
| EP | 2 896 458 A1 | | 7/2015 |
| EP | 2 918 343 | | 9/2015 |
| WO | 03/060512 | | 7/2003 |
| WO | 2005-515439 | | 5/2005 |
| WO | WO 2013/111025 | | 8/2013 |
| WO | WO2013111025 | * | 8/2013 |

OTHER PUBLICATIONS

Office Action dated Mar. 27, 2019 in Chinese Application No. 201580079052.5 with English translation, 16 pages.
Office Action dated Jan. 25, 2019 in Japanese Application No. 2017-554460, with translation, 10 pages.
Translation of EP 2 660 602, previously cited on an IDS filed on Oct. 2, 2017.

* cited by examiner

INCUBATION TRAY

The present invention relates to an incubation tray having a depression formed by the walls of the incubation tray, and comprising a base, wherein the incubation tray comprises a means for drawing off liquid at at least one longitudinal end of the depression, preferably an opening which opens into an outlet channel on the longitudinal end of the depression, particularly preferably in a wall of the incubation tray, wherein the opening and the outlet channel are designed in such a way that negative pressure can be applied, wherein the incubation tray is pivotable about the transverse axis of the incubation tray, and wherein the incubation tray can be equipped with a carrier.

Pathological and laboratory diagnostic tests are an indispensible foundation of modern medicine. A plurality of tests that can be carried out on a routine basis have become available, with the aid of which decisive information regarding the present clinical picture, the prognosis, or the success of a therapy can be obtained from sample material in the absence of the patient.

In this case, patient samples in the form of tissue sections or cells can be initially stained, and the stained structures can then be tested within the framework of performing a diagnosis. In the field of histology or histopathology, in particular, stained tissue sections only a few micrometers thick are prepared and are evaluated under the microscope.

Sample material utilized in histological work primarily includes surgical specimens, exploratory excisions, and tissue removed by means of biopsies, wherein the primary goal of the testing of tissue sections stained in this manner is to reliably detect and type tumors. With the aid of such methods, tissue can be histologically characterized and cancer can be diagnosed by way of the investigations of growths and tumors.

Alternatively, patient samples can be tested for the presence or the concentration of certain molecules when the values obtained provide information that is useful, on the basis of reference data, for the diagnosis. In this way, the detection of specific autoantibodies can indicate that the patient is suffering from an autoimmune disease. Examples of autoimmune diseases include infections, inflammatory diseases such as rheumatoid diseases, metabolic disorders such as diabetes, and neurological diseases.

One unsolved problem is the scarcity and high prices of reagents and sample material. Working sequences and material consumption are optimized in order to increase cost-effectiveness. In particular, there is a trend toward miniaturization: diagnostic, pathohistological, and analytical reactions are no longer carried out in the scale of milliliters, but rather microliters and even nanoliters. This saves reagents and space and makes it possible for a sample, which has been collected one time, to provide a sufficient amount of starting material for a large number of diagnostic tests. Last but not least, the patient is spared the experience of having another sample taken even in the event that a single diagnostic test fails.

One particular problem associated with miniaturization is that the ratio of the fluid volume retained due to capillary forces and adhesion on surfaces, on the one hand and, on the other hand, the total volume of the fluid utilized for one method step is particularly high. In other words, so much fluid adheres to the surfaces that the fluid cannot be efficiently removed by being poured off or by pipetting after a method step.

A relatively large volume of the fluid remains, which adversely affects the subsequent method step. For example, a remaining wash solution dilutes a reagent that has been introduced for a subsequent reaction and thereby reduces the yield or sensitivity of the subsequent reaction.

US 2014/248618 describes an arrangement for a microfluidic flow cell which, however, is not pivotable and is also not an incubation tray, but rather a closed system. The same applies for the microscopy device described in U.S. Pat. No. 6,673,620.

One problem addressed by the present invention is therefore that of providing a method, by means of which samples to be pathologically or laboratory diagnostically analyzed can be analyzed using the smallest possible amount of reagents and sample. In particular, the problem is that of increasing the concentration of the reagents while using a given absolute quantity.

Short reaction times and a high quality of the stainings, in particular due to a continuous convection of the liquid phase, are also to be ensured. Time-consuming and error-prone manual steps during the staining are to be largely avoided.

Yet another problem addressed by the present invention is that of reducing the space required, the loss of fluid, and/or the duration of the conversion or of the entire assay as compared to the methods described in the prior art. At the same time, the reproduciblity is to be maintained or increased.

Yet another problem is that of providing a method which minimizes the risk of mistakes and an associated waste of reagents and damage to the sample.

This and further problems are solved by the subject matter of the present application and, in particular, by the subject matter of the attached independent claims, wherein embodiments result from the dependent claims.

The problem addressed by the invention is solved, in a first aspect, by an incubation tray having a depression formed by the walls of the incubation tray, and comprising a base, wherein the incubation tray comprises a means for drawing off liquid at at least one longitudinal end of the depression, preferably an opening which opens into an outlet channel on the longitudinal end of the depression, particularly preferably in a wall of the incubation tray, wherein the opening and the outlet channel are designed, preferably in a pressure-tight manner, in such a way that negative pressure can be applied, wherein the incubation tray is pivotable about the transverse axis of the incubation tray, and wherein the incubation tray can be equipped with a carrier.

In one preferred embodiment of the first aspect, negative pressure is applied via the outlet channel.

In yet another preferred embodiment, the suction means enables the fluid on the base to be drawn off and is preferably an opening which opens into an outlet channel and is located on the base of the incubation tray.

In yet another preferred embodiment, the incubation tray has an opening which opens into an outlet channel, which opening opens into an outlet channel extending on the plane of the base or therebelow, which outlet channel adjoins an outlet compartment which is separated from the depression and has an outlet compartment opening.

In yet another preferred embodiment, the incubation tray contains a carrier including a biological sample which is preferably situated on the side of the carrier that faces the base of the incubation tray, wherein the carrier preferably lies on the base.

In yet another preferred embodiment, the incubation tray contains a fluid, wherein the incubation tray preferably has an opening which opens into an outlet channel and the surface of the fluid preferably lies above the opening.

In yet another preferred embodiment, the carrier and the incubation tray are matched to each other in such a way that the carrier can be moved in the depression, back and forth along the longitudinal axis of the incubation tray, when the incubation tray is equipped with the carrier.

In yet another preferred embodiment, the incubation tray furthermore has an opening which opens into the inlet channel, preferably in a wall of the incubation tray that adjoins an inlet compartment which is separated from the depression, which inlet compartment has an inlet compartment opening, wherein the inlet channel preferably extends along the longitudinal axis of the incubation tray, on the plane of the base or therebelow.

In yet another preferred embodiment, the incubation tray comprises an opening which opens into an outlet channel, along the longitudinal axis of the incubation tray at one longitudinal end, and has an opening which opens into an inlet channel, at the other longitudinal end of the depression.

In the ninth preferred embodiment, which is also an embodiment of the third to eighth embodiments, the incubation tray further includes an extraction hood which is detachably fitted on the outlet compartment opening and comprises an outgoing line, via which negative pressure can be applied.

In the tenth preferred embodiment, which is also a preferred embodiment of the first to ninth embodiments, the carrier can be moved, during the movement, up to one longitudinal end of the depression and thereby gaplessly abuts the longitudinal end of the depression.

The problem addressed by the invention is solved, in a second aspect, by a device comprising a lower part including incubation trays according to the invention, each of which has at least one outlet compartment opening and an extraction hood comprising a frame-shaped upper part, wherein the lower part and the upper part are matched to each other in such a way that the upper part can be placed onto the lower part in such a way that an extraction hood is fitted on each outlet compartment opening.

The problem addressed by the invention is solved, in a third aspect, by a method for incubating a carrier, including the steps:

a) incubating a carrier, in the presence of a fluid, in the depression of an incubation tray having a depression formed by the walls of the incubation tray, and comprising a base, and b) drawing off the fluid at one longitudinal end of the depression, preferably via an opening which opens into an outlet channel which is under negative pressure, wherein the opening is located at the longitudinal end of the depression, preferably on the base of the incubation tray, and wherein the incubation tray is an incubation tray according to the invention, according to the first aspect, or an incubation tray in the device according to the second aspect.

In a first preferred embodiment of the third aspect, the incubation tray is pivotable about the transverse axis of the incubation tray and at least one of the steps a) and b), preferably step b), is carried out during pivoting.

In a second preferred embodiment of the third aspect, step b) is carried out in the instant at which an incubation tray is pivoted in such a way that a fluid located therein collects at the longitudinal end of the incubation tray—preferably in the largest possible quantity—at which the fluid is drawn off, and in which the carrier has preferably moved up to this longitudinal end of the depression and, particularly preferably, gaplessly abuts the longitudional end of the depression.

The present invention relates to an incubation tray at which, according to the invention, a negative pressure is applied in order to remove fluid. The incubation tray is designed in such a way that fluid residue can also be removed in this way, which would not be removed by way of an exclusively gravity-driven pouring off. The fluid is therefore removed more efficiently than is the case with conventional incubation trays and methods.

In one preferred embodiment, the incubation tray is longitudinal, i.e. the ratio of the shorter side to the longer side, which defines the longitudinal axis, is 1 at least 1, for example 1:1.25, 1:1.5, 1:1.61, 1:1.75, 1:1.86, 1:2, 1:2.5, 1:2.923, 1:3, 1:4, 1:5, 1:5.2, 1:7.5 or 1:10. The incubation tray is fluid-tight. It can be provided with a cover, a film, or a similar covering. The incubation tray can be insertable, in the form of an introduceable insert, into a tablet matched thereto, which can contain a plurality of incubation trays, e.g. at least 2, 3, 4, 5, 6, 10, 12, 15, 20 or 30 incubation trays. In one preferred embodiment, the tablet can accommodate multiple incubation trays of different sizes.

The base of the incubation tray is flat and forms a plane. Nevertheless, this does not need to be a plane without any types of irregularities; instead, the base can be provided with grooves or roughened portions. If a structural feature is described as being located "under" or "over" the base, its plane or a plane that is parallel to this plane, the position is therefore meant to be vertical relative to this plane.

The incubation tray can be equipped with a carrier. This is preferably a flat carrier matched to the width of the incubation tray, preferably a glass carrier, more preferably a biochip of the type described, for example, in DE 20 2011 005 278. The carrier can be transparent. It can be directly coated with a sample, although it is also possible to apply the sample itself on a further object carrier, for example a film or a thin glass or plastic disk which is bonded onto the transparent object carrier or is fastened thereto in another way. The carrier can have properties and characteristics of the type described in EP14152113.8. Preferably, the sample is situated on the underside of the carrier, i.e. the side facing the base of the incubation tray.

The incubation tray and the carrier can be matched to each other in such a way that the incubation carrier can be equipped with the carrier. Preferably, the incubation tray and the carrier are elongate, wherein the length of the carrier is less than the length of the depression, and so the carrier placed into the depression does not touch the two longitudinal ends of the depression. The length of the carrier is preferably 50 to 99, more preferably 50 to 95, even more preferably 60 to 90 percent of the length of the depression. The width of the carrier is preferably selected in such a way that the carrier introduced into the depression cannot rotate on the base of the incubation tray.

The carrier introduced into the depression is preferably unfastened and can move, preferably along the longitudinal axis, during the pivoting of the incubation tray having the carrier and fluid therein, within the framework of the geometric boundaries defined by the walls of the depression. Preferably, the shape of the incubation tray and the carrier are matched to each other in such a way that one end of the carrier gaplessly abuts the longitudinal end of the depression when the incubation tray is pivoted in such a way that the carrier moves up to the end of the depression and rests on the longitudinal end of the depression. The gapless abutment does not need to extend across the entire width of the carrier, but it suffices in order to at least partially channel fluid that is located under the carrier or that is flowing under the carrier, in the direction of the outlet compartment opening.

Alternatively, the carrier can be a test strip and/or a suitable membrane, for example a nitrocellulose membrane, coated with samples or diagnostic reagents.

In one particularly preferred embodiment, the carrier lies on the base of the depression in such a way that, after filling with a fluid, the carrier is at least partially undercoated with the fluid, and so a sample on the carrier is in contact with the fluid. The carrier can lie directly on the base, or the incubation tray and/or the carrier has a means for fixing a separation, preferably the minimum separation, between the underside of the carrier and the base of the depression. For example, one foot or more than one foot can be installed on the underside of the carrier, for example a base or one rail or more than one rail, optionally in the form of a pair arranged in parallel, for example installed in parallel to the longitudinal direction of the carrier, on the side thereof facing the base, made from the same material as the carrier. Alternatively, a frame can lie on or be installed on the base of the incubation tray or on the walls, on which frame the carrier rests at a fixed distance from the base of the depression. The necessary local fluid exchange can also be ensured in another way, e.g. in that the incubation tray is moved in a regular manner and the carrier is displaced at least briefly or floats without rotating.

The means for fixing the distance ensures, particularly when the sample is situated on the underside of the carrier, that the sample is in contact with fluid especially when the carrier is not completely covered. In addition, this arrangement effectuates the formation of a separate compartment which is closed on the bottom by the base, on the top by the underside of the carrier, and on the side by the walls, the contents of which can be particularly effectively drawn off through an opening in the base of the incubation tray. In this case, fluid is also removed that adheres on the carrier or the incubation tray, due to an interaction with surfaces, and would not be removed by pouring off. In addition, the evaporation of the fluid and, therefore, the consumption of reagents, is reduced by means of the compartment.

In one particularly preferred embodiment, the sample is diagnostically or analytically processed. This preferably means that the sample has been treated using diagnostic methods and/or agents in such a way that the state of the sample—optionally after further processing steps—allows for an analysis and a contribution to a diagnosis. Options include, for example, laboratory medical, cytological, morphological-microscopic, biochemical, (immuno) chemical, in particular immunohistochemical or enzyme histochemical, molecular biological, histological, serological, pathological, chemical, or physical analytical methods.

In one particularly preferred embodiment, the sample is a biological sample which is embedded in paraffin and/or is fixed in formaldehyde solution. In one particularly preferred embodiment, a tissue section is stained using dyes or marked antibodies, preferably fluorescence-marked antibodies, and is investigated using light microscopy with respect to the morphology of the cells contained therein. Exemplary molecular biological methods include in situ hybridizations such as fluorescence in situ hybridization. Examples of pathological methods include stainings such as ATPase-, NADH-, hematoxylin-/eosin-, Gomori's trichrome-, PAS-, and oil red staining on muscle biopsies. Suitable reagents, software, and devices for processing samples are commercially available, for example from the company EUROIMMUN AG Medizinische Labordiagnostika, Lübeck.

The biological sample can be selected, for example, from the group including tissue, preferably tissue sections or tissue biopsies, e.g. frozen sections, biological cells such as eukaryotic or prokaryotic cells or products thereof, viruses, purified, isolated or synthetically produced molecules such as nucleic acids, polypeptides, lipids, or carbohydrates. The biological sample is preferably of human or animal origin.

The incubation tray comprises an outlet channel having an outlet channel opening for the removal of fluid from the incubation tray via suction which is selected in such a way that the carrier is not removed or damaged during the suctioning. In one preferred embodiment, this is a tube, the end of which is inserted into the fluid. Preferably this is a channel which is integrated into the incubation tray. Pressure can be applied to the outlet channel for suctioning.

The width of the outlet channel is preferably 50% to 100%, more preferably 60% to 95%, even more preferably 75% to 95% of the width of the depression of the incubation tray or the carrier, preferably of the carrier.

Preferably, the outlet channel opens into an outlet compartment having an outlet compartment opening. This is a space, preferably along the longitudinal axis of the incubation tray at one end thereof, which is closed with respect to pressure and fluid loss, except for the mouth of the channel and the opening, and in which fluid contained in the incubation tray can collect when the incubation tray is appropriately tilted, without being in contact with the carrier. The outlet compartment opening is designed in such a way that an extraction device, preferably an extraction hood, can be detachably or fixedly installed. The base of the outlet compartment can lie at least partially below the plane of the base of the depression, in order to support the fluid flow into the compartment. The term "extraction hood", as used herein, is preferably understood to be a round lower part, preferably at least on the base, made from a flexible material, for example a rubber or plastic suction cup, which is fitted on the opening in a pressure-tight manner and into which an outgoing line is formed, via which pressure is applied.

Proceeding from the plane of the base, the opening of the outlet channel is vertically arranged in such a way that at least one part of the opening, preferably the entire opening, lies below the surface of a fluid which fills the incubation tray, more preferably is filled so far that the carrier is just completely covered with fluid. The opening is preferably located on the base. This is the case when all the fluid located in the incubation tray can run out, except for residue adhering to surfaces, when the tray is tilted in such a way that the fluid runs in the direction of the opening.

In one preferred embodiment, the outlet channel is under negative pressure which is preferably dimensioned in such a way that fluid in the depression is drawn out. The delivery rate at which the fluid is drawn out can be 0.1 l/min to 10 l/min, preferably 0.2 l/min to 5 l/min, even more preferably 0.3 l/min to 3 l/min. Conventional devices can be utilized for the suctioning, for example, diaphragm pumps, gear pumps, piston pumps, or peristalic pumps. The suctioning of the fluid can take place continuously or discontinuously. In one preferred embodiment, the suctioning takes place continuously, i.e. the majority of the fluid is not drawn out all at once, for example at the end of the incubation process, but rather in multiple steps. Particularly preferably, in one method step which includes the incubation of the carrier in a fluid, fluid is simultaneously introduced at one end of the incubation tray and is drawn off at the other end of the incubation tray at at least one point in time, preferably at least 10, 20, 30, 60, 120, 300, 600 seconds, 10, 15, 20 or 30 minutes long. In this way, the carrier only ever comes into contact with unused, fresh fluid. This accelerates the processing of the carrier or the biological sample. In yet another preferred embodiment, after the fluid is introduced, the carrier is initially incubated therein, preferably at least 10, 20, 30, 60, 120, 300 seconds, 10, 15 or 30 minutes long, before the fluid is drawn off.

The incubation tray can be filled with a fluid, preferably an aqueous fluid, more preferably a wash buffer or a reagent for processing a sample on the carrier. The volume of the fluid is dimensioned in such a way that the biological sample is in sufficient contact therewith. In one preferred embodiment, the volume of the fluid in the incubation tray is dimensioned in such a way that the fluid completely covers the carrier and the sample thereon in the horizontal position. In yet another preferred embodiment, the volume of the fluid in the incubation tray is dimensioned in such a way that the fluid completely covers a sample which is situated on the side of the carrier facing the base. In yet another preferred embodiment, the volume of the fluid in the incubation tray is dimensioned in such a way that it does not continuously wet the sample, but rather regularly, when the incubation tray is pivoted during incubation. While readily available solutions such as non-specific wash buffers, for example PBS, or solutions for developing a signal, can be utilized in excess, the user is limited to using the absolutely necessary minimum volumes of other solutions, such as reagents that are difficult to obtain and are only available in small volumes, such as antibodies, in particular primary antibodies.

Optionally, the incubation tray comprises an inlet channel. This is a closed means for the inflow of fluid, which does not need to be designed to be pressure-tight. The inflow can take place directly into the incubation tray or via an inlet compartment opening in an inlet compartment, preferably along the longitudinal axis at the end of the incubation try, preferably at the end opposite the outlet compartment. The base of the inlet compartment can lie at least partially below the plane of the base of the depression, in order to reduce the local pressure generated by incoming fluid droplets.

The incubation tray can preferably be moved in such a way that the fluid is mixed and its exposure to the carrier is promoted, for example by pivoting, vibration, shaking, or the like. In one preferred embodiment, the incubation tray is pivotable about the transverse axis of the incubation tray, and so the fluid moves in the direction of the lower lying longitudinal end of the incubation tray. In the pivoted state, particularly when the outlet opening is located at the longitudinal end and the outlet channel opening is located on the base thereof, the removal of the fluid is particularly simple and efficient. During pivoting, the incubation tray forms an angle with the base surface of 1° to 45°, preferably 2.5° to 30°, more preferably 7.5° to 25°.

The invention is described in the following with reference to the figures on the basis of exemplary embodiments. The embodiments described are to be considered, in every respect, to be merely examples and not to be restrictive, and different combinations of the mentioned features are included in the scope of the invention.

Figure 1:
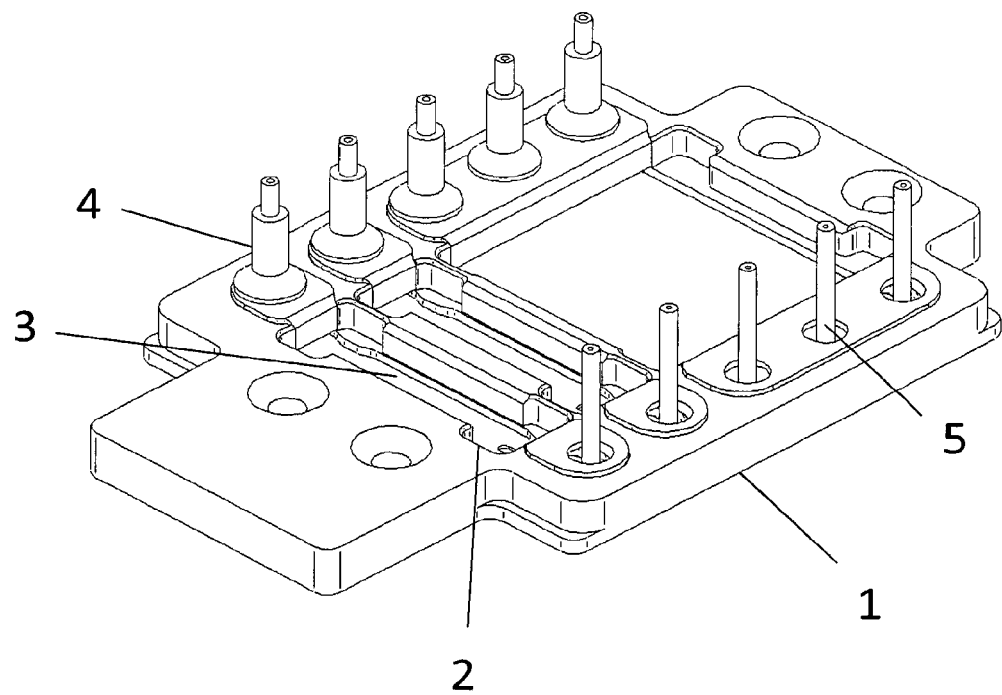
FIG. 1 shows a device according to the invention, including a lower part (1) comprising an incubation tray (2) located therein, which incubation tray includes a depression (3), an extraction hood (4) on the outlet compartment, and an inlet channel (5) which leads into the inlet compartment.
Figure 2A:
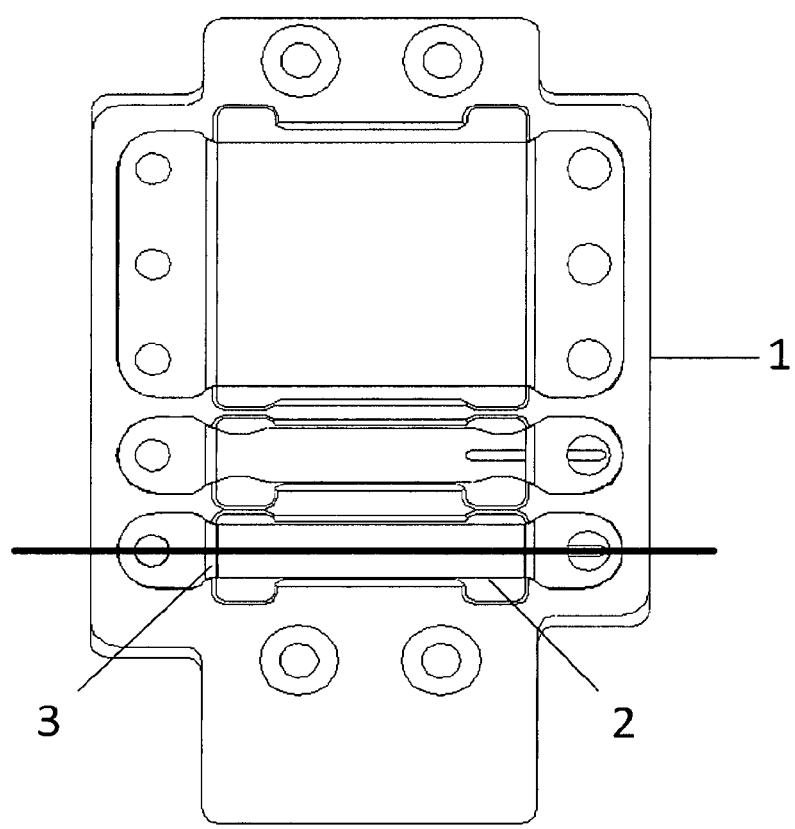
FIG. 2A shows a device according to the invention from above, including a lower part (1) and an incubation tray (2) including a depression (3). The black bar marks the point at which the cross section of the device represented in FIG. 2B lies.
Figure 2B:
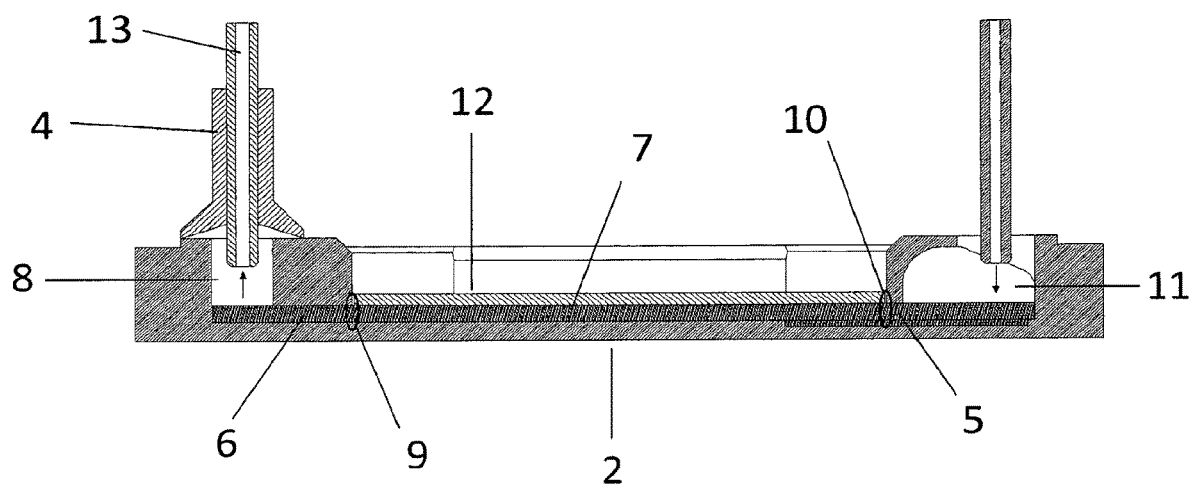

FIG. 2B shows a cross section of the device according to the invention, through an incubation tray (2), at the point marked in FIG. 2A with the aid of a black bar. Located at one end along the longitudinal axis of the incubation tray is an outlet compartment (8) which is connected via an outlet channel (6) to the depression filled with a fluid (7). A fluid can be drawn out of the outlet compartment via an outgoing line (13) located in the extraction hood (4) by applying a negative pressure. Fluid can be introduced into the inlet compartment (11) via an inlet channel (5). The inlet channel (5) and the outlet channel (6) open into the depression in the form of an inlet compartment opening (10) or outlet compartment opening (9), respectively. A carrier including a biological sample (12) is immersed into the fluid. In FIG. 2B, the base of the inlet compartment (11) lies below the plane of the base of the depression.

The different subfigures of FIG. 3 shows the interaction of a device according to the invention, comprising a lower part (1, 14), with an upper part (15) matched thereto. Only the lower part is shown in FIG. 3A.

Figure 3A:
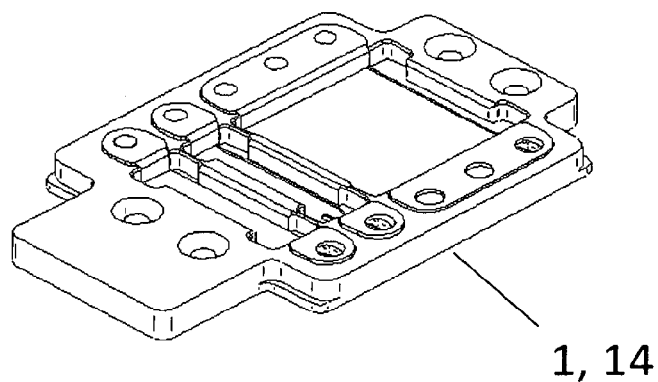
Figure 3B:
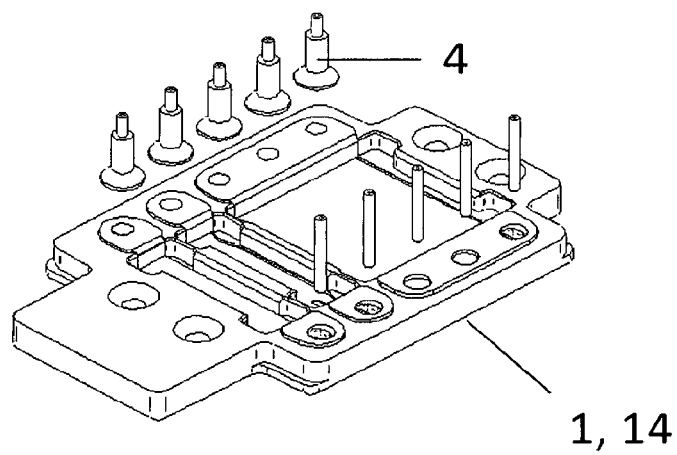

In FIG. 3B, the lower part is shown together with a set of extraction hoods (4) and a set of inlet channels (5).

Figure 3C:
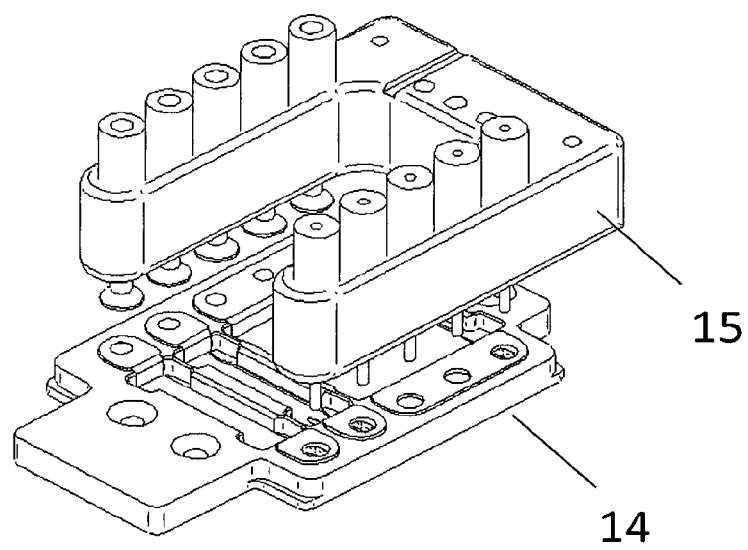

FIG. 3C shows the upper part (15) and the lower part (14), wherein the upper part is equipped with extraction hoods and inlet channels which are arranged in such a way that they can be fitted onto the outlet compartment openings and inlet compartment openings, respectively.

Figure 3D:
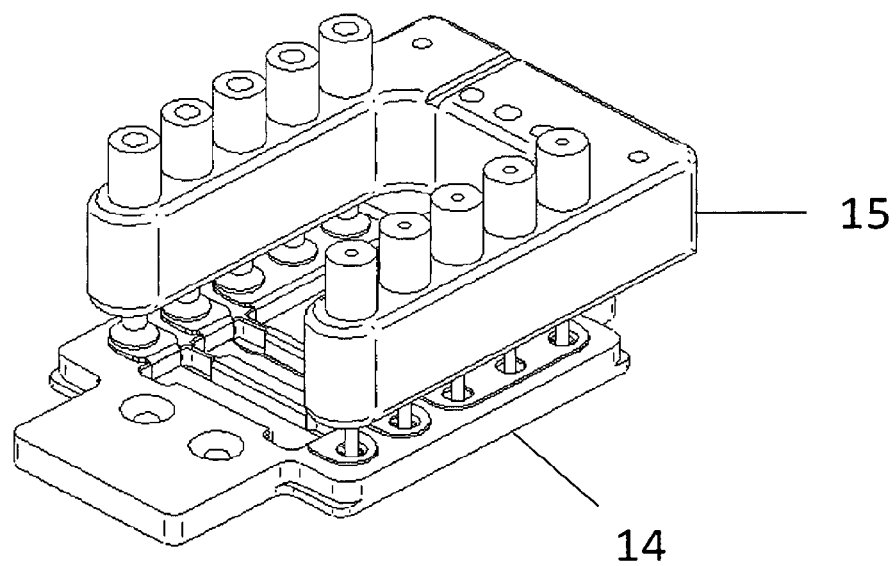

FIG. 3D shows the same device according to the invention as FIG. 3C, except that the upper part (15) has been fitted on the lower part (14).

Figure 4A:
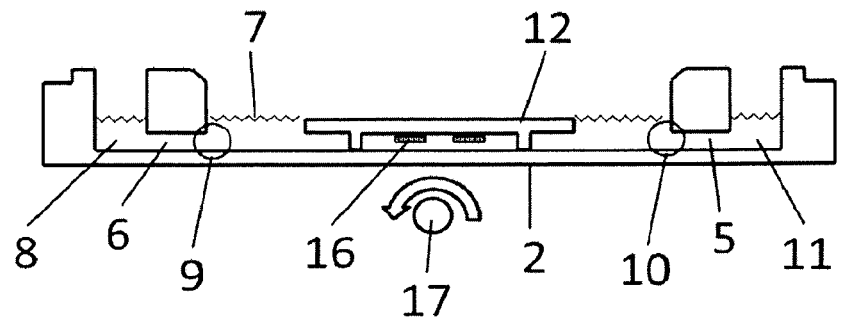

FIG. 4A shows an incubation tray (2) which is filled with a fluid (7) and has a depression (3) which is equipped with a carrier including a biological sample (12). The sample (16) is located on the carrier on the side thereof facing the base of the incubation tray. The carrier can be moved in the incubation tray, back and forth along the longitudinal axis, in particular by way of the incubation tray being pivoted via a rotational axis (17) about the transverse axis (not shown, parallel to the rotational axis). The carrier stands via two feet on the base, which feet are designed in such a way that fluid can flow past them along the longitudinal axis.

Figure 4B:
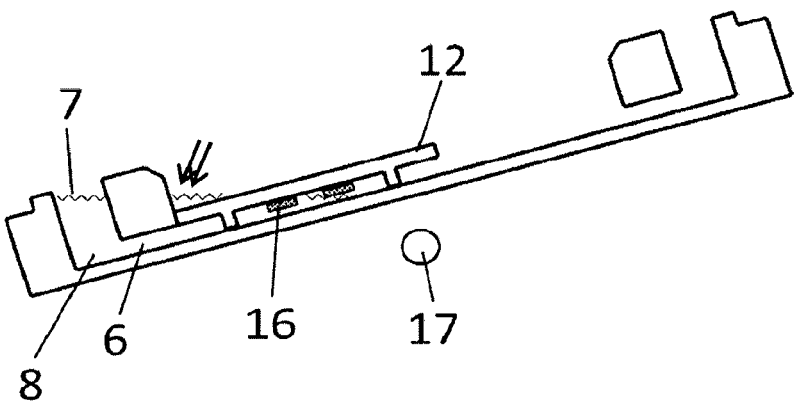

FIG. 4B shows the same device after the pivoting about the transverse axis. The carrier (12) including the biological sample (16) moves, together with the fluid and under the force of gravity, up to the longitudinal end of the depression of the incubation tray, wherein the carrier gaplessly abuts the longitudinal end of the depression (marked with a double arrow). The fluid collects at the longitudinal end of the depression or the incubation tray that is pivoted downward.

Figure 4C:
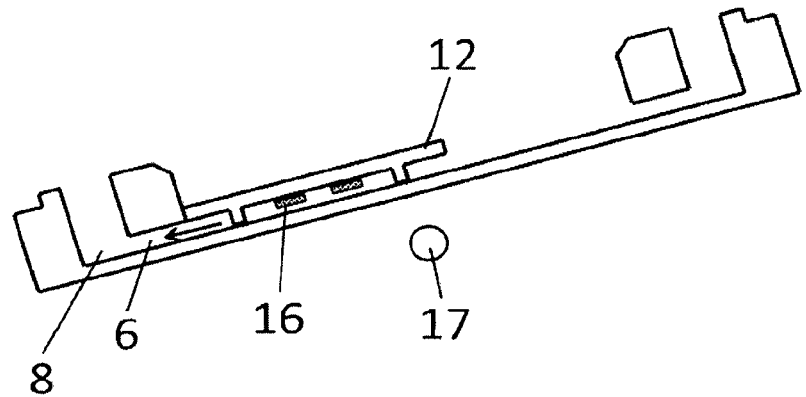

FIG. 4C shows that the carrier, the base, and the walls of the incubation tray form a channel in this situation, through which the fluid can be particularly efficiently drawn off through the outlet channel (6) when a negative pressure is applied in the outlet compartment. The flow of the fluid through the channel is marked using a single arrow. No fluid remains at the longitudinal end.

LIST OF REFERENCE NUMBERS 1 device comprising a lower part
2 incubation tray
3 depression
4 extraction hood
5 inlet channel
6 outlet channel
7 fluid
8 outlet compartment 9 outlet compartment opening
10 inlet compartment opening
11 inlet compartment
12 carrier including biological sample
13 outgoing line
14 lower part
15 upper part
16 sample
17 rotational axis

The invention claimed is:

1. An incubation tray, comprising:
a depression formed by walls of the incubation tray,
a base,
an opening which opens into an outlet channel, along the longitudinal axis of the incubation tray at one longitudinal end, and
an opening which opens into an inlet channel, at the other longitudinal end of the depression
wherein said opening into said outlet channel allows for drawing off liquid from at least one longitudinal end of the depression,
wherein the incubation tray is pivotable about the transverse axis of the incubation tray,
wherein the incubation tray is equipped with a carrier comprising a biological sample which is situated on a side of said carrier which is arranged facing a bottom of said incubation tray and which is in direct contact with said carrier, and
wherein said incubation tray or said carrier comprises a means for fixing a separation between said bottom of said incubation tray and said side of said carrier which is facing said bottom and defining a space between said bottom of said incubation tray, said side of said carrier which is facing said bottom and said walls of said incubation tray.

2. The incubation tray as claimed in claim 1,
wherein negative pressure is applied via said outlet channel.

3. The incubation tray as claimed in claim 1,
wherein a suction means allows a fluid on the base to be drawn off.

4. The incubation tray as claimed in claim 1,
wherein said outlet channel adjoins an outlet compartment which is separated from the depression and has an outlet compartment opening.

5. The incubation tray as claimed in claim 1,
containing a fluid.

6. The incubation tray as claimed in claim 1,
wherein the carrier and the incubation tray are matched to each other in such a way that the carrier can be moved in the depression, back and forth along the longitudinal axis of the incubation tray.

7. The incubation tray as claimed in claim 4,
further including an extraction hood which is detachably fitted on said outlet compartment opening and comprises an outgoing line, via which negative pressure can be applied.

8. The incubation tray as claimed in claim 6,
wherein the carrier can be moved, during the movement, up to one longitudinal end of the depression and thereby gaplessly abuts the longitudinal end of the depression.

9. A device, comprising:
a lower part comprising incubation trays each having at least one outlet compartment opening, and a frame-shaped upper part including extraction hoods as claimed in claim 7,
wherein the lower part and the upper part are matched to each other in such a way that the upper part can be placed onto the lower part in such a way that each extraction hood is fitted on each outlet compartment opening.

10. A method for incubating a carrier, comprising:
a) incubating a carrier, in the presence of a fluid, in the depression of an incubation tray having a depression formed by the walls of the incubation tray, and comprising a base, and
b) drawing off the fluid at one longitudinal end of the depression,
wherein an opening is located at the longitudinal end of the depression,
and wherein the incubation tray is as claimed in claim 1.

11. The method as claimed in claim 10,
wherein the incubation tray is pivotable about the transverse axis of the incubation tray and at least one of the steps a) and b) is carried out during pivoting.

12. The method as claimed in claim 11,
wherein step b) is carried out in the instant at which said incubation tray is pivoted in such a way that said fluid located therein collects at the longitudinal end of the incubation tray at which the fluid is drawn off.

13. The incubation tray of claim 1, comprising:
an opening for drawing off liquid, wherein the opening opens into an outlet channel on the longitudinal end of the depression, wherein the opening and the outlet channel are designed in such a way that negative pressure can be applied.

14. The incubation tray of claim 1,
wherein the opening opens into an outlet channel on the longitudinal end of the depression in a wall of the incubation tray, wherein the opening and the outlet channel are designed in such a way that negative pressure can be applied.

15. The incubation tray of claim 1, wherein in a first position, said incubation tray is parallel to horizontal and in a second position, said incubation tray is at an angle to horizontal.

16. The incubation tray of claim 1, wherein, said opening is in a wall of the incubation tray that adjoins an inlet compartment which is separated from the depression, wherein said inlet compartment has an inlet compartment opening.

* * * * *